United States Patent
Kim et al.

(10) Patent No.: US 7,068,828 B2
(45) Date of Patent: Jun. 27, 2006

(54) BIOCHIP IMAGE ANALYSIS SYSTEM AND METHOD THEREOF

(75) Inventors: Jin Hyuk Kim, Seongnam (KR); Yong Sung Lee, Seoul (KR); Young Seek Lee, Seoul (KR)

(73) Assignee: Gaiagene Inc., Seoul (KR)

( * ) Notice: Subject to any disclaimer, the term of this patent is extended or adjusted under 35 U.S.C. 154(b) by 675 days.

(21) Appl. No.: 10/305,106

(22) Filed: Nov. 27, 2002

(65) Prior Publication Data

US 2003/0113004 A1 Jun. 19, 2003

Related U.S. Application Data

(60) Provisional application No. 60/352,964, filed on Jan. 30, 2002.

(30) Foreign Application Priority Data

Nov. 29, 2001 (KR) .............................. 2001-074811

(51) Int. Cl.
*G06K 9/00* (2006.01)
(52) U.S. Cl. ...................... 382/129; 382/128
(58) Field of Classification Search ................ 382/128, 382/129, 130, 131, 132, 133, 134, 199, 266, 382/269; 435/6, 69.1, 91.4, 477, 252.3, 333; 436/94, 508; 800/25; 514/44
See application file for complete search history.

(56) References Cited

U.S. PATENT DOCUMENTS

| | | | |
|---|---|---|---|
| 6,081,612 A | * | 6/2000 | Gutkowicz-Krusin et al. ........................ 382/128 |
| 6,448,012 B1 | * | 9/2002 | Schwartz ...................... 435/6 |
| 6,897,026 B1 | * | 5/2005 | Lamont et al. ................ 435/6 |
| 6,980,677 B1 | * | 12/2005 | Niles et al. ................. 382/128 |

\* cited by examiner

*Primary Examiner*—Jingge Wu
*Assistant Examiner*—Abolfazl Tabatabai
(74) *Attorney, Agent, or Firm*—Harness, Dickey & Pierce, P.L.C.

(57) ABSTRACT

A biochip image analysis system comprises an image storage unit storing image information including an original image of the biochip including genes extracted from experimental and control groups' samples tagged by fluorescent dyes of different colors; an image converter converting the original image into a test image, generating an overlapped image and a color image; an edge detector separating spots of the test image into segments and detecting edges from spot and background areas to measure expression degrees of genes; a blob detector detecting blobs from the spot and background areas to generate a blob template; a blob remover generating a spot template and a background template; a data processor calculating statistical data and correcting intensity; and a data storage unit storing the data.

12 Claims, 6 Drawing Sheets

(A)　　　　　(B)　　　　　(C)

BIOCHIP IMAGE ANALYSIS SYSTEM AND METHOD THEREOF

This application claims benefit of Provisional Application No. 60/352,964 filed Jan. 30, 2002.

BACKGROUND OF THE INVENTION (a) Field of the Invention

The present invention relates to a biochip image analysis system and method thereof. More specifically, the present invention relates to an image analysis system and method for detecting an edge of a cDNA (complementary deoxyribonucleic acid) chip and removing blobs that cause data errors.

(b) Description of the Related Art

Biochips include glass or nylon wafer membranes designed for accelerating genetic research, they are designed for providing a plurality of short DNA strands and essential genetic information for determining living creatures' characteristics on a single substrate, and they are frequently used as test beds for chemical samples.

Biochips may accelerate checking of about 30,000 genes in human DNA, and progression of current global coordinated research thereof, the so-called human genome project, for making a human genome map.

Biochips are classified into protein chips, oligonucleotide chips, and cDNA chips.

Regarding protein chips, dozens to hundreds of different proteins or ligands are provided on the chip surface in a micro-array format. In this instance, when a sample is added to the protein chip, biomolecules specifically interactive with the proteins or ligands provided on the chip surface remain, and others are washed away.

Existence states or functions of the above interactive biomolecules are analyzed using an SPR (surface plasmon resonance) device, a mass spectrometer, or a fluorescence spectrometer. The protein chips may be effectively applied to cancers, AIDS (acquired immune deficiency syndrome), early diagnosis of human diseases, causal examination of diseases, and understanding of in vivo signal transduction systems.

Oligonucleotide chips use 25 oligonucleotides to search for mutations of specified genes. That is, oligonucleotide chips adopt a photolithography method to synthesize oligonucleotides of a desired nucleotide sequence on a slide glass, and they search for mutations of tumor suppressive genes such as p53 and BRCA1 using the synthesized oligonucleotides.

Oligonucleotide chips may be applied to inherited disorder fields including gene mutation detection, drug resistance detection diagnosis, SNP (single nucleotide polymorphism) analysis, histocompatibility and organ transplantation assays, identification of pathogenic microorganisms, nucleotide sequence analysis, paternity tests, interracial polymorphism analysis, and forensic medicine.

As for cDNA chips, thousands to tens of thousands of genes are formed as predetermined-sized spots on a predetermined slide glass substrate to create a cDNA micro-array, fluorescent labeling is performed on mRNAs (messenger ribonucleic acids) of two groups to be compared, that is, the mRNA of a control group and that of an experimental group, and they are competitively combined to the cDNA chip so as to check relative gene expression patterns.

The cDNA micro-array chips generated in this manner contribute greatly to analysis of particular genes expressed in specific cells or tissues. The cDNA micro-array chips may be used for high throughput gene expression—analysis, human disease diagnosis and monitoring, biological response studies of environmental factors, food inspection, new drug development, clinicopathology, and for animal and plant quarantine.

A method for manufacturing the above-noted cDNA micro-array chips will now be described.

Test genes are planted on a glass slide in a spot format having a predetermined size to thereby generate arrays comprising thousands to tens of thousands of spots.

Messenger RNAs are extracted from samples of a control group and an experimental group to perform reverse transcription on the mRNAs, and in this instance, dyes having fluorescence of red Cy5 or green Cy3 are provided to the mRNAs to tag the mRNAs.

In this instance, genes expressed in yellow are provided by superposing green and red, and it is found that similar amounts of the above-noted genes are expressed under the two environments.

The synthesized mRNAs of the two samples are mixed in identical amounts to thus hybridize them on an array chip, uncombined genes are washed from the chip, and hybridized genes remain thereon to generate a cDNA micro-array chip.

The cDNA micro-array chip is read by a laser fluorescent scanner. In this instance, the fluorescent images of the cDNA micro-array chip are scanned by each 5 μm or 10 μm-sized diameter pixel. The fluorescent images are stored in a computer in a 16-bit image format, and fluorescence intensities of the respective genes represent the genes' expression levels, and the levels are analyzed by a computer.

When analyzing cDNA micro-array images, since the cDNA micro-array chip has cDNA of different genes formed as spots of 100 μm~250 μm diameters that are printed on a glass slide, the respective spots are separated into segments so as to measure expression degrees of the respective genes.

In this instance, a reference circle of a predetermined size is positioned on the center of the segment so as to extract an effective spot, and if the size of the reference circle is greater than that of the spot, the background as well as the spot are positioned within the reference circle, and accordingly, errors occur in data mean values.

In another case, when the center of the spot is not located on the center of the segment but it digresses to a side, since the positions of the reference circle and the spot are not matched, a portion of the spot located in the reference circle is used as effective information, and the remaining spots are processed as a background to thereby increase data error rates.

Blobs or streaks are generated on the segments of the cDNA micro-array chip because of artifacts or other factors provided from the outside, and the blobs or streaks change the mean value and the standard deviation of the intensity of the spots or the background because of the very high intensities of the blobs, and accordingly, if the blobs are not removed, erroneous data may be obtained.

Further, since the images obtained by a scanning process via the fluorescent scanner and other types of images generated from various converting and analyzing processes occupy a very large part of the memory capacity, the time spent for outputting desired images on a screen or analyzing data may be very much longer.

SUMMARY OF THE INVENTION

It is an object of the present invention to provide a biochip image analysis system and method for extracting edge information used for analyzing gene information of a cDNA chip, removing the blobs such as artifacts and bubbles that cause data errors to reduce data error rates, and solving the declination problem of calculation speed generated when processing a huge volume of information.

In one aspect of the present invention, a biochip image analysis system comprises: an image storage unit for storing information on various types of images including an original image of a biochip including a set of genes extracted from samples of an experimental group and a control group each tagged by fluorescent dyes of different colors; an image converter for converting the original image stored in the image storage unit into a test image, generating an overlapped image and a color image from the test image, and storing the respective images in the image storage unit; an edge detector for separating spots of the test image stored in the image storage unit into segments and detecting edges from a spot area and a background area so as to measure expression degrees of respective genes; a blob detector for detecting blobs and streaks from the spot area and the background area detected by the edge detector to generate a blob template; a blob remover for using the blob template generated by the blob detector to generate a spot template from which the blobs are removed and a background template; a data processor for calculating statistical data and correcting intensity on the basis of the spot template and the background template generated by the blob remover; and a data storage unit for storing the statistical data output by the data processor.

The test image of the image converter is an 8-bit image to be provided to a user at a predetermined time.

A pseudo color red is provided to a first test image, and a pseudo color green is provided to a second test image from among the two test images, caused by fluorescent dyes of different colors, and the two test images to which the colors are provided are overlapped to generate the color image of the image converter.

The system comprises an input/output unit for outputting the images or the data generated by or stored in the image storage unit, the edge detector, the blob remover, and the data storage unit to a screen according to requests by the user.

A biochip image analysis method comprises: (a) extracting an original image according to fluorescent dyes of different colors from a biochip including a set of specific genes expressed from an experimental group and a control group tagged by the fluorescent dyes; (b) converting the original image into a test image, and generating an overlapped image and a color image from the test image; (c) separating a spot into segments, detecting a spot area and a background area from each segment, and detecting spot and background edges so as to measure expression degrees of genes corresponding to the respective spots on the test image; (d) detecting blobs and streaks from the spot and background areas to generate a blob template, and using the blob template to generate a spot template from which the blobs are removed and a background template, when the edges are detected; and (e) calculating statistical data and correcting intensity on the basis of the spot template, the background template, and the blob template generated through (b) to (d).

The (e) comprises outputting the images or the data generated through (b) to (d) to a screen according to requests by a user.

The (d) comprises: performing a logical AND operation on the spot area extracted from the overlapped image and the template obtained by inverting the 15 blob template to thereby generate a spot template from which the blobs are removed; and performing a logical AND operation on the background area and the template obtained by inverting the blob template to thereby generate a background template from which the blobs are removed.

The (d) comprises: (1) separating respective spots from the test image including spots to generate the spots' segment coordinates; (2) extracting a segment of an $N^{th}$ coordinate's spot to generate a spot edge and a background edge; (3) transplanting the spot edge and the background edge onto an empty template, and detecting blobs from an area within each edge to generate a blob template; and (4) using the blob template to remove the blobs from the spot and background areas, repeating the edge detection process, the blob detection process, and the blob removal process from the subsequent (N+1) coordinate to the final coordinate to thereby generate a final spot template and a background template.

The (3) comprises: (A) calculating a mean intensity and a standard deviation from the segments of each spot of the overlapped image, and collecting them; (B) separating the pixels in the segment on the test image into a predetermined number of clusters according to the pixel intensity, the number being suitable for detecting the blobs; (C) using the mean intensity and the standard deviation to calculate a first critical value, and comparing the first critical value with a second critical value, the second critical value being set as a lower critical value of the first critical value and the cluster having the maximum mean intensity; (D) setting a final critical value according to a comparison result, substituting a first substitution value for the intensity values of the pixels greater than the final critical value, and a second substitution value for the intensity values of the pixels less than the final critical value to thereby set a blob area; (E) measuring a length ratio of the blob area's area and width to obtaining the blobs that satisfy the standard set by a system; and (F) generating the image extracted from (E) as a blob template, and storing the same.

In (C), the first critical value is obtained by adding a mean intensity to a product of the standard deviation and a data option assigned by the user.

In (C), when the first critical value is greater than the second critical value, an empty image is stored as a blob template.

In (D), the first substitution value is 0×FF, and the second substitution value is 0×00.

BRIEF DESCRIPTION OF THE DRAWINGS

The accompanying drawings, which are incorporated in and constitute a part of the specification, illustrate an embodiment of the invention, and, together with the description, serve to explain the principles of the invention.

DETAILED DESCRIPTION OF THE PREFERRED EMBODIMENTS

In the following detailed description, only the preferred embodiment of the invention has been shown and described, simply by way of illustration of the best mode contemplated by the inventor(s) of carrying out the invention. As will be realized, the invention is capable of modification in various obvious respects, all without departing from the invention. Accordingly, the drawings and description are to be regarded as illustrative in nature, and not restrictive.

Figure 1:
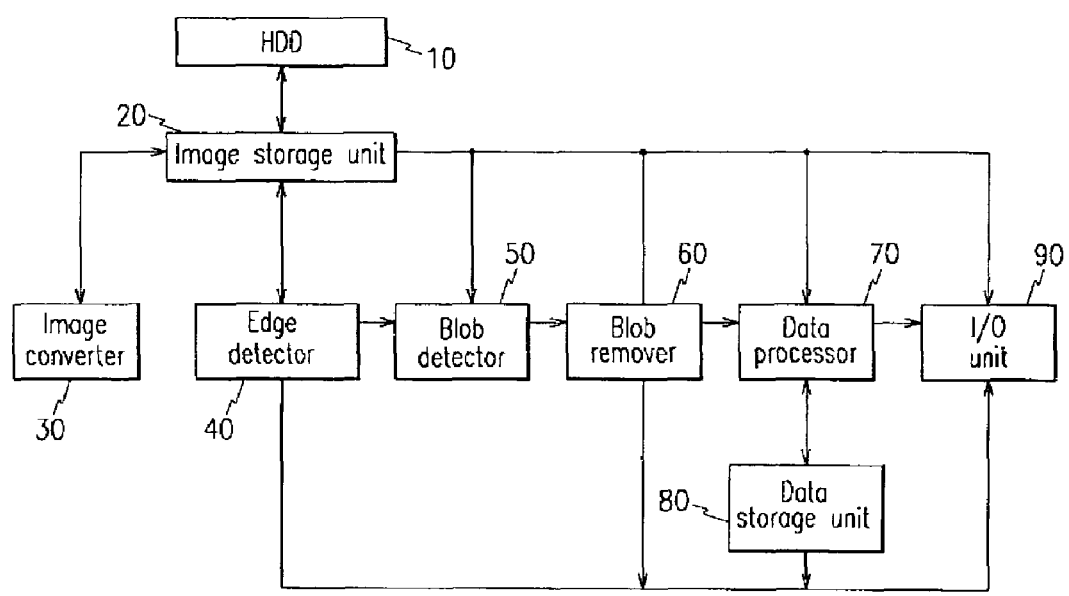
FIG. 1 shows a block diagram of a biochip's image analysis system according to a preferred embodiment of the present invention.

FIG. 1 shows a block diagram of a biochip's image analysis system according to a preferred embodiment of the present invention.

As shown, the system comprises: an image storage unit 20 for storing original images, and various converted images generated from the original images, the original images being obtained by scanning two cDNA micro-array images and being stored in a HDD (hard disk drive) 10 in the 16-bit TIFF (tag image file format) format; an image converter 30 for converting the original images stored in the image storage unit 20 into test images, generating overlapped images and color images from the test images, and storing the overlapped images and the color images in the image storage unit 20; an edge detector 40 for separating spots into segments so as to measure expression degrees of the genes corresponding to the respective spots of the overlapped images stored in the image storage unit 20, and detecting edges in a spot area and a background area in each segment; a blob detector 50 for detecting blobs in the spot areas and the background areas stored in the image storage unit 20 to generate a blob template; a blob remover 60 for using the blob template generated by the blob detector to remove the blobs from the spot areas and the background areas; a data processor 70 for calculating statistical data and correcting the intensity on the basis of a spot template and a background template generated through the blob remover 60; a data storage unit 80 for storing the statistical data generated by the data processor 70; and an I/O (input/output) unit 90 for reading the 16-bit original images, and displaying the images and the data stored in the image storage unit 20, the edge detector 40, the blob remover 60, and the data storage unit 80 on the screen according to a request by a user.

In this instance, the image converter 30 converts the 16-bit original images by Cy3 and Cy5 into 8-bit test images and overlapped images so as to increase the image processing speed and provide the images to the user at a suitable time.

In general, the cDNA micro-array chip scans twice with lasers of two different wavelengths so as to find the Cy3 and Cy5 fluorescent dyes, and the positions of the cDNA micro-array chip may be mismatched with each other because of many factors during the two scanning operations.

Hence, the image converter 30 performs automated position correction for matching the positions of the two images before processing the images, and generates an overlapped image of the two images.

Also, the image converter 30 provides the 8-bit Cy3 image with pseudo green, and the 8-bit Cy5 image with pseudo red, and overlaps them to generate a color image.

A cDNA micro-array image represents a scanned image on which respective cDNAs of different genes are printed in a spot form of a diameter of substantially 100 to 150 µm, and the image includes approximately 10,000 spots, the number of which may be varied according to chip categories.

Therefore, the edge detector 40 performs a segmentation process for separating each spot into segments so as to measure expression degrees of the genes corresponding to the spots, and detects spot areas and background areas on the segment to detect spot edges and background edges.

In this instance, a segment coordinate of the spot is stored in an array format, and index information for each segment is input.

In the above, the spot's index information is generated by classifying the cDNA micro-array chip into a plurality of sub-grids, by generating a column index and a row index of each sub-grid, and by generating a column index and a row index of a segment of each spot in a sub-grid.

For example, the spot's index information is generated in the (a, b, c, d) format, and the 'a' and the 'b' represent column and row indexes of the sub-grid, and the 'c' and the 'd' indicate column and row indexes of a spot in the corresponding sub-grid.

The blob detector 50 separates the intensities of all pixels in each segment by a number of clusters suitable for detecting the blobs that cause data errors, such as particles, bubbles, and big and small lumps.

The blob detector 50 sets a blob area according to a first critical value determined by a mean intensity, a standard deviation, and a data option (which is an alpha) assigned by the user, and a second critical value determined by a bottom critical value of a cluster having a maximum mean intensity, measures a ratio of a length to the area and the width of the blob area, and only filters the blobs that satisfy a standard set by the system to thereby generate a blob template.

The blob remover 60 uses the blob template obtained from the blob detector 50 to calculate a spot area and a background area and generate a spot template and a background template from which the blobs are removed.

The data processor 70 calculates various measurement values such as a mean intensity, a mean value, a standard deviation, a central value, a mode, a spot area and circumference, a number of holes in a spot, and a segmentation state as statistical data from the 16-bit original images on the basis of the spot template and the background template obtained from the blob remover 60, and stores them in the data storage unit 80. In this instance, the statistical data may be linked to the spot's index information.

The fluorescent dyes Cy3 and Cy5 have different sensitivities to the fluorescence, and the RNA samples are tagged with the fluorescent dyes Cy3 and Cy5 by identical amounts, but it is impossible to use exactly identical amounts of the RNAs and the fluorescent dyes Cy3 and Cy5.

Therefore, the data processor 70 performs a normalization process for correcting a state where the luminance of an image is more strongly measured than that of the other image.

The I/O unit 90 displays the images and the data stored in the image storage unit 20, the edge detector 40, the blob remover 60, the data processor 70, and the data storage unit 80 on the screen according to a request by the user.

An operation of the biochip image analysis system as configured above will now be described with reference to drawings.

Figure 2:
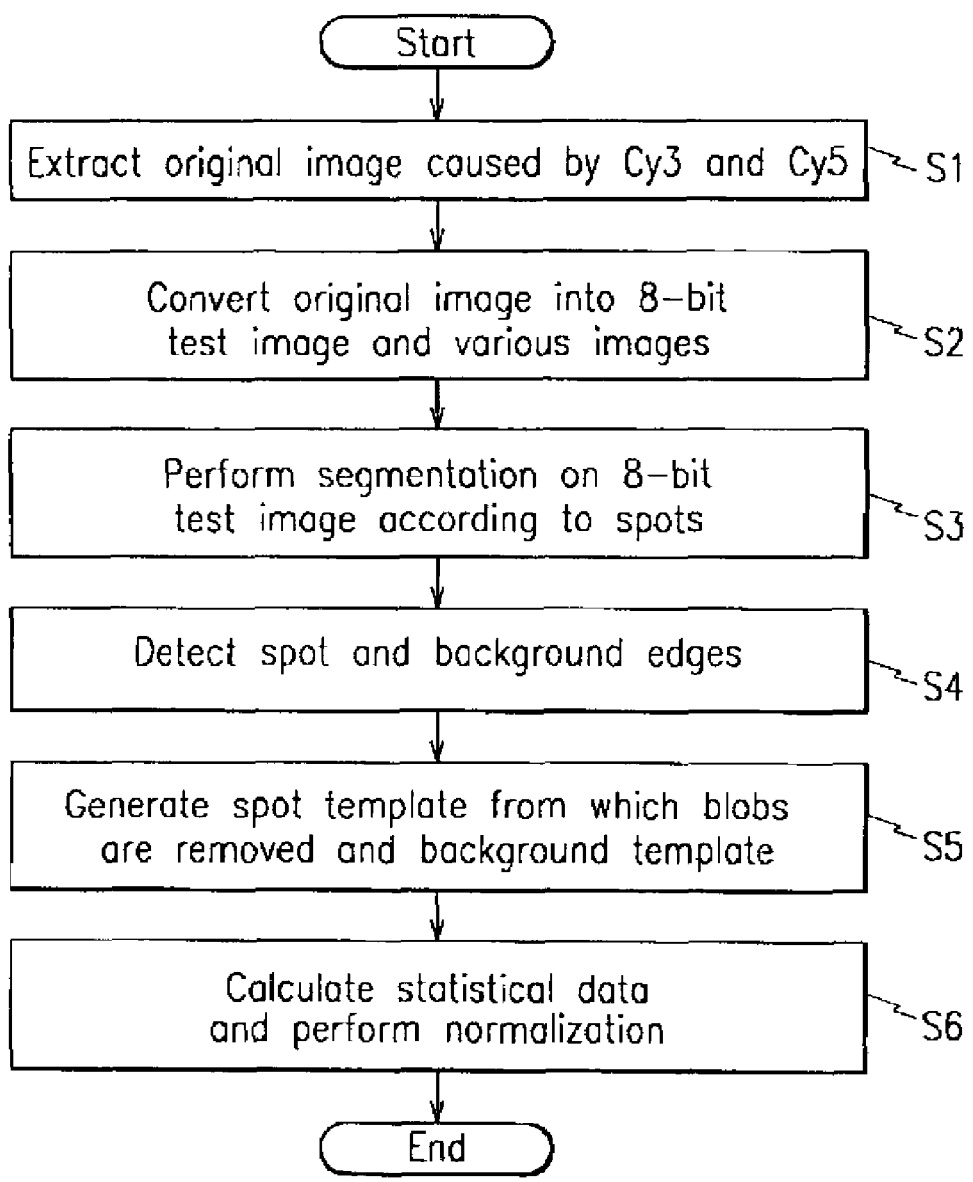
FIG. 2 shows a flowchart of a biochip's image analysis method according to a preferred embodiment of the present invention.

FIG. 2 shows a flowchart of a biochip's image analysis method according to a preferred embodiment of the present invention.

Referring to FIG. 2, original images in the 16-bit TIFF format are extracted from the HDD 10, and they are stored in the image storage unit 20 in step S1.

The image converter 30 converts the two original images into 8-bit test images, and generates an overlapped image from the two images to configure a color image to be displayed to a user in step S2.

The edge detector 40 separates the spots of the test image into segments so as to measure the expression degrees of the genes corresponding to each spot, and stores the spot's segment coordinate as an array format in step S3, and detects the spot area and the background area of each segment to detect edges of the spot and the background in step S4.

The blob detector 50 measures the intensity to detect the blobs and thereby generate a blob template, and the blob remover 60 removes the blobs from the spot area and the background area to generate a spot template and a background template in step S5.

The data processor 70 generates, from the 16-bit original images, statistical data on the basis of the spots and the background templates acquired from the above process, and it performs data normalization for correcting the intensities of the two images caused by Cy3 and Cy5 in step S6.

Figure 3:
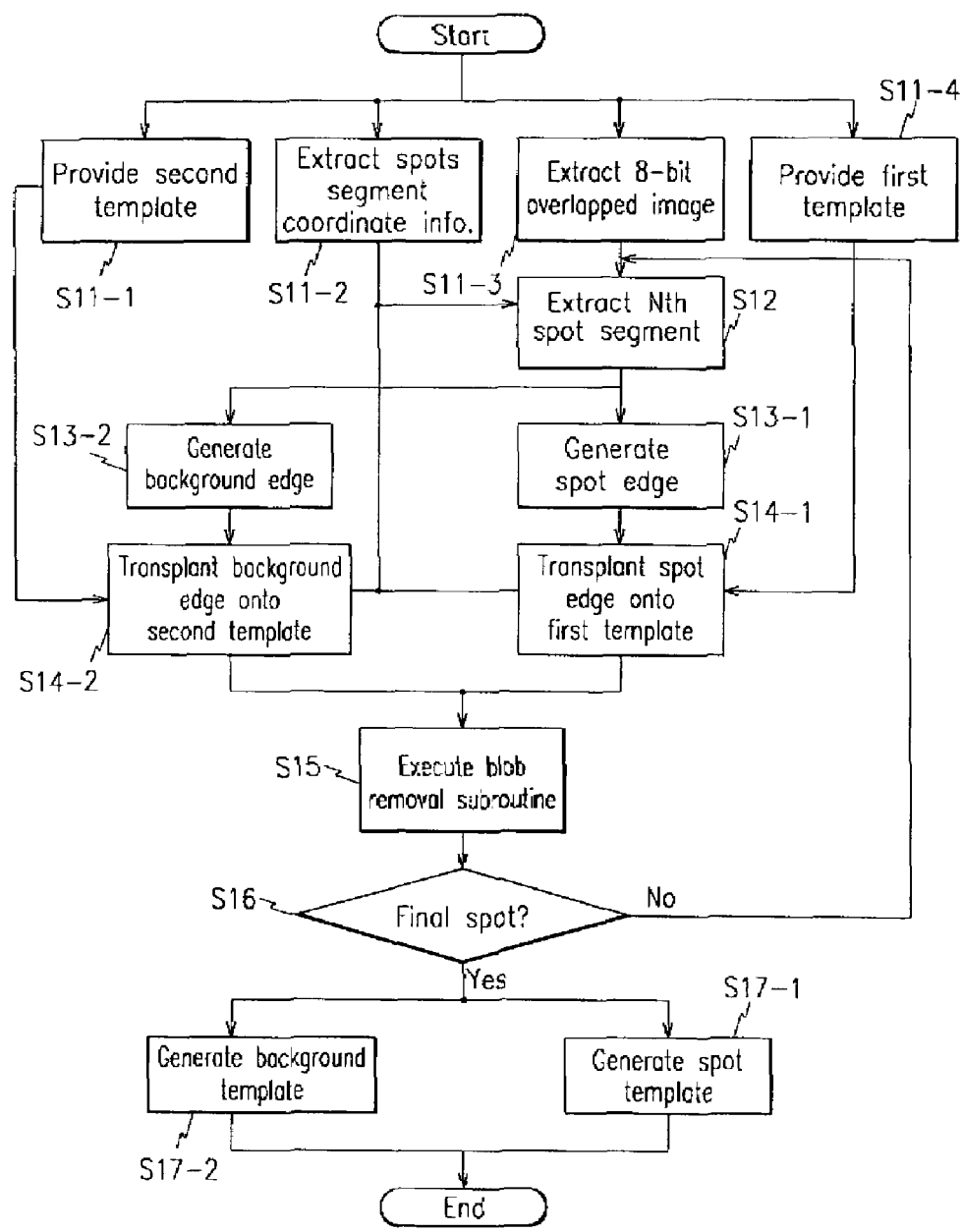
FIG. 3 shows a flowchart of an image processing stage of the biochip's image analysis method according to a preferred embodiment of the present invention.

FIG. 3 shows a flowchart of an image processing stage of the biochip image analysis method according to a preferred embodiment of the present invention.

As shown, the edge detector 40 provides an 8-bit empty first template provided for a spot template and an 8-bit second template provided for a background template in steps S11-4 and S11-1, and calls an overlapped 8-bit image and segment coordinate data of the spots by segmentation from the image storage unit 20 and the data storage unit 80 in steps S11-3 and S11-2.

The edge detector 40 uses the spot's segment coordinate and the overlapped 8-bit image to extract an $n^{th}$ spot segment in step S12, and generates in steps S13-1 and S13-2 a spot edge and a background edge from the spot segment extracted from the above process.

When generating the spot edge and the background edge, the edge detector 40 transplants the spot edge onto the first template in step S14-1, and the background edge onto the second template in step S14-2.

The blobs of relative brightness intensities on the respective templates on which the spot edges and the background edges are transplanted, heavily influence statistics of the spots and the background. Therefore, the blob detector 50 and the blob remover 60 perform a subroutine for accurately perceiving the blobs and removing them to increase the accuracy of the statistics of the spots and the background in step S15.

It is determined whether the spot in the segment is a final spot according to segment coordinate information in step S16. When the spot is not the final spot, the edge detector 40 goes to the previous step S12, and repeats the process for extracting the $(N+1)^{th}$ spot segment and generating a spot template and a background template. When the spot is the final spot, the edge detector 40 completes the generation of the spot template and the background template in steps S17-1 and S17-2.

Figure 4:
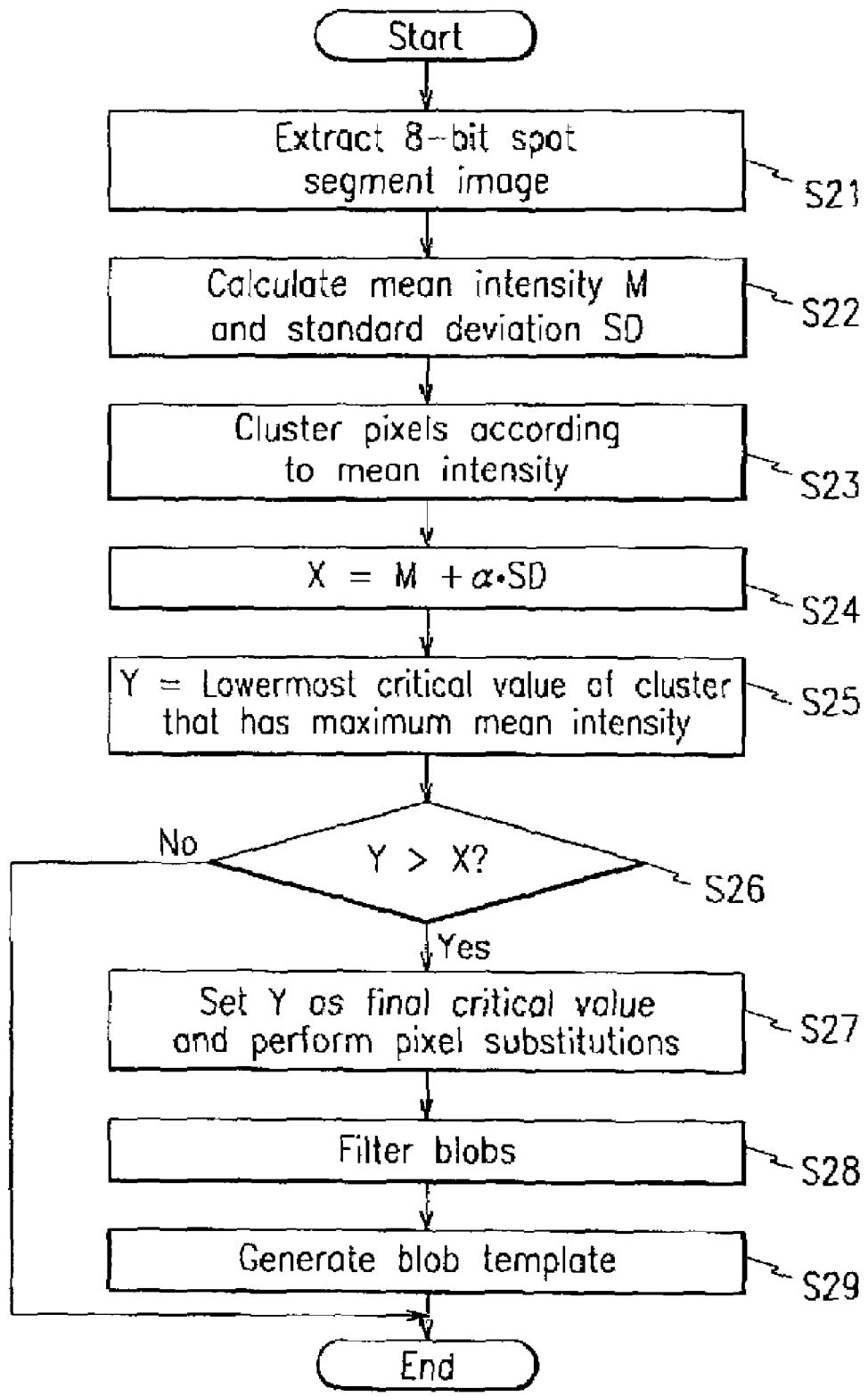
FIG. 4 shows a flowchart for executing a blob removing subroutine according to a preferred embodiment of the present invention.

FIG. 4 shows a flowchart for executing a blob removing subroutine according to a preferred embodiment of the present invention.

As shown, the blob detector 50 calls segment images of each spot from the 8-bit overlapped image in step S21, and it calculates a mean intensity M and a standard deviation SD from the spot's segment images in step S22.

After this, the blob detector 50 separates all the pixels in the segment images of the spot into a number of clusters most suitable for detecting the blobs according to the mean intensity in step S23, and it adds the mean intensity to the product of the data option (which is the alpha) assigned by the user and the standard deviation to calculate a first critical value X in step S24. That is, X=M+alpha×SD.

The blob detector 50 also sets the lowermost critical value of the cluster that has the maximum mean intensity from among the clusters separated from the above as a second critical value Y in step S25.

When the first and second critical values are set as described above, the blob detector 50 determines whether the second critical value is greater than the first critical value in step S26. When the second critical value is greater than the first critical value, the blob detector 50 sets the second critical value as a final critical value, and substitutes the first substitution value 0×FF for the intensity values of pixels greater than the second critical value, and the second substitution value 0×00 for the intensity values of pixels less than the second critical value from among the respective pixels in the segment image to thereby set a blob area in step S27.

The blob detector 50 measures the area and the ratio of a width to a height of the blob area from the image on which the blob area is set, and filters the blobs that satisfy the standard preset by the system in step S28.

The blob detector 50 generates a blob template from the image generated through the blob detection process, and stores the blob template in the image storage unit 20 in step S29. When the second critical value is less than the first critical value, the blob detector 50 stores an empty blob template in the image storage unit 20.

Figure 5:
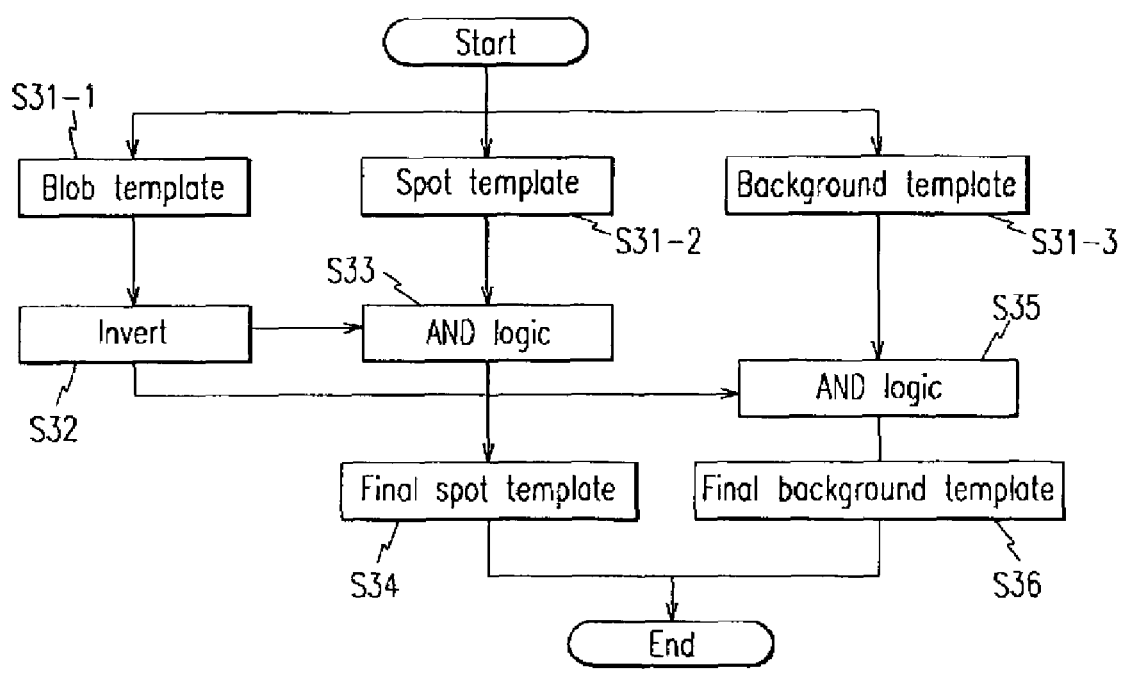
FIG. 5 shows a flowchart for generating a final spot template and a background template.
Figure 6:
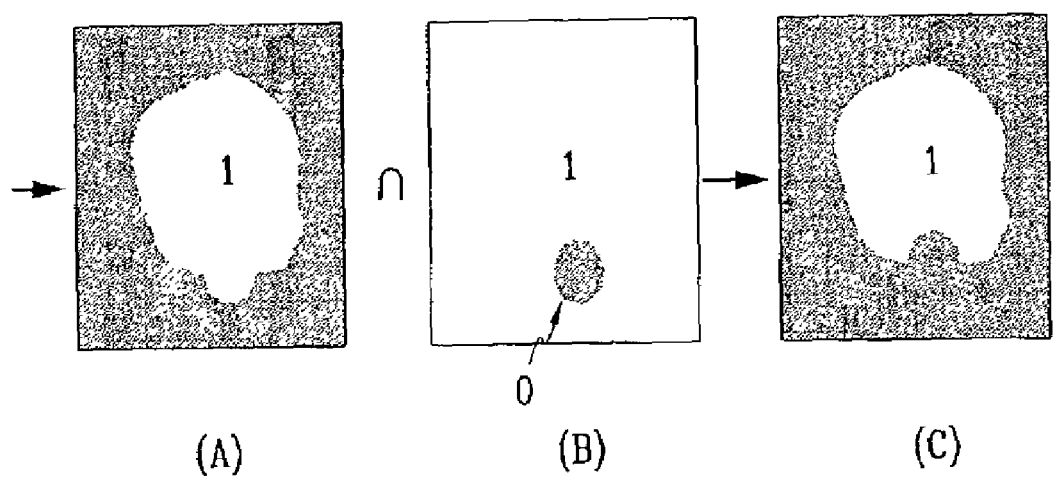
FIG. 6 shows a template configuration for generating a final spot template.

FIG. 5 shows a flowchart for generating a final spot template and a background template, and FIG. 6 shows a template configuration used for generating a final spot template.

As shown in FIG. 5, the blob remover 60 provides a blob template, a spot template, and a background template generated by the edge detector 40 and the blob detector 50 in steps S31-1, S31-2, and S31-3.

The blob remover 60 inverts the blob template to substitute 0×00 for the intensity value of the blob, and 0×FF for the intensity value of the remaining background in step S32, and passes the inverted blob template and the spot template through an AND logic in step S33 to generate a final spot template in step S34.

That is, as shown in FIG. 6, an AND operation is performed on the spot template A and a template B that is an inverted blob template to generate a final spot template C from which the blobs are removed.

In the like manner as described above, as to the final background template, the inverted blob template and the background template are passed through the AND logic in step S35 to generate the final background template from which the blobs are removed and which has effective information in step S36.

In the case of analyzing gene information of a cDNA micro-array chip from among various types of biochips, the biochip image analysis system and method according to the present invention generates a spot's segment coordinate on the gene chip comprising a spot group in a two-dimensional array format, detect spot and background edges, and links indexes of each segment and data to provide effective information to the user.

Also, the present invention detects blobs such as particles and bubbles that cause data errors, thereby greatly reducing data error rates and enabling extraction of effective information.

In addition, the present invention solves the problem of lowering of calculation speed generated according to processing a great volume of information when calculating data from an image including more than ten thousand chips.

While this invention has been described in connection with what is presently considered to be the most practical and preferred embodiment, it is to be understood that the invention is not limited to the disclosed embodiments, but, on the contrary, is intended to cover various modifications and equivalent arrangements included within the spirit and scope of the appended claims.

What is claimed is:

1. A biochip image analysis system comprising:
   an image storage unit for storing information on various types of images including an original image of a biochip including a set of genes extracted from samples of an experimental group and a control group, each tagged by fluorescent dyes of different colors;
   an image converter for converting the original image stored in the image storage unit into a test image, generating an overlapped image and a color image from the test image, and storing the respective images in the image storage unit;
   an edge detector for separating spots of the test image stored in the image storage unit into segments and detecting edges from a spot area and a background area so as to measure expression degrees of respective genes;
   a blob detector for detecting blobs from the spot area and the background area detected by the edge detector to generate a blob template;
   a blob remover for using the blob template generated by the blob detector to generate a spot template from which the blobs are removed and a background template;
   a data processor for calculating statistical data and correcting intensity on the basis of the spot template and the background template generated by the blob remover; and
   a data storage unit for storing the statistical data output by the data processor.

2. The system of claim 1, wherein the test image of the image converter is an 8-bit image to be provided to a user at a predetermined time.

3. The system of claim 1, wherein a pseudo color red is provided to a first test image, and a pseudo color green is provided to a second test image from among the two test images, caused by fluorescent dyes of different colors, and the two test images to which the colors are provided are overlapped to generate the color image of the image converter.

4. The system of claim 1, comprising an input/output unit for outputting the images or the data generated by or stored in the image storage unit, the edge detector, the blob remover, and the data storage unit to a screen according to requests by the user.

5. A biochip image analysis method comprising:
   (a) extracting an original image according to fluorescent dyes of different colors from a biochip including a set of specific genes expressed from an experimental group and a control group tagged by the fluorescent dyes;
   (b) converting the original image into a test image, and generating an overlapped image and a color image from the test image;
   (c) separating a spot into segments, detecting a spot area and a background area from each segment, and detecting spot and background edges so as to measure expression degrees of genes corresponding to the respective spots on the test image;
   (d) detecting blobs from the spot and background areas to generate a blob template, and using the blob template to generate a spot template from which the blobs are removed and a background template, when the edges are detected; and
   (e) calculating statistical data and correcting intensity on the basis of the spot template, the background template, and the blob template generated through (b) to (d).

6. The method of claim 5, wherein (e) comprises outputting the images or the data generated through (b) to (d) to a screen according to requests by a user.

7. The method of claim 5, wherein (d) comprises:
   performing a logical AND operation on the spot area extracted from the overlapped image and the template obtained by inverting the blob template to thereby generate a spot template from which the blobs are removed; and
   performing a logical AND operation on the background area and the template obtained by inverting the blob template to thereby generate a background template from which the blobs are removed.

8. The method of claim 5, wherein (d) comprises:
   (1) separating respective spots from the test image including spots to generate the spots' segment coordinates;
   (2) extracting a segment of an $N^{th}$ coordinate's spot to generate a spot edge and a background edge;
   (3) transplanting the spot edge and the background edge onto an empty template, and detecting blobs from an area within each edge to generate a blob template; and
   (4) using the blob template to remove the blobs from the spot and background areas, repeating the edge detection process, the blob detection process, and the blob removal process from the subsequent (N+1) coordinate to the final coordinate to thereby generate a final spot template and a background template.

9. The method of claim 8, wherein (3) comprises:
   (A) calculating a mean intensity and a standard deviation from the segments of each spot of the overlapped image, and collecting them;
   (B) separating the pixels in the segment on the test image into a predetermined number of clusters according to the pixel intensity, the number being suitable for detecting the blobs;
   (C) using the mean intensity and the standard deviation to calculate a first critical value, and comparing the first critical value with a second critical value, the second critical value being set as a lower critical value of the first critical value and the cluster having the maximum mean intensity;
   (D) setting a final critical value according to a comparison result, substituting a first substitution value for the intensity values of the pixels greater than the final critical value, and a second substitution value for the intensity values of the pixels less than the final critical value to thereby set a blob area;
   (E) measuring a length ratio of the blob area's area and width to obtaining the blobs that satisfy the standard set by a system; and
   (F) generating the image extracted from (E) as a blob template, and storing the same.

10. The method of claim 9, wherein in (C), the first critical value is obtained by adding a mean intensity to a product of the standard deviation and a data option assigned by the user.

11. The method of claim 9, wherein in (C), when the first critical value is greater than the second critical value, an empty image is stored as a blob template.

12. The method of claim 9, wherein in (D), the first substitution value is 0×FF, and the second substitution value is 0×00.

* * * * *